United States Patent [19]

Horodysky et al.

[11] Patent Number: 4,536,306

[45] Date of Patent: Aug. 20, 1985

[54] BORATED PHOSPHORUS-CONTAINING COMPOUNDS AND LUBRICANT COMPOSITIONS CONTAINING SAME

[75] Inventors: Andrew G. Horodysky, Cherry Hill; Phillip S. Landis, Woodbury, both of N.J.

[73] Assignee: Mobil Oil Corporation, New York, N.Y.

[21] Appl. No.: 561,410

[22] Filed: Dec. 14, 1983

[51] Int. Cl.³ .......................... C10M 1/44; C10M 1/54
[52] U.S. Cl. .............................. 252/32.7 E; 252/49.9; 260/922; 260/980; 260/462 R
[58] Field of Search .......................... 252/32.7 E, 49.9; 260/922, 980, 462

[56] References Cited

U.S. PATENT DOCUMENTS

| | | | |
|---|---|---|---|
| 2,978,478 | 4/1961 | Sandner et al. | 252/49.9 |
| 3,083,223 | 3/1963 | Wright | 252/49.9 |
| 3,795,612 | 3/1974 | Stournas | 252/49.9 |
| 4,118,329 | 10/1978 | Holten | 252/49.9 |
| 4,229,310 | 10/1980 | Frangatos | 252/49.9 |

Primary Examiner—Jacqueline V. Howard
Attorney, Agent, or Firm—Alexander J. McKillop; Michael G. Gilman; Van D. Harrison, Jr.

[57] ABSTRACT

Certain diol-phosphorus oxyhalide-boron compound reaction products have been found to have antioxidant and antifriction properties and to hinder the corrosion of copper surfaces.

27 Claims, No Drawings

BORATED PHOSPHORUS-CONTAINING COMPOUNDS AND LUBRICANT COMPOSITIONS CONTAINING SAME

BACKGROUND OF THE INVENTION

1. Field of the Invention

This invention relates to friction reducing additives for lubricants and liquid fuels. More particularly, the invention relates to lubricant and fuel compositions to which has been added a borated phosphorus-containing compound.

2. Discussion of the Prior Art

The metal surfaces of machinery or engines operating under heavy or normal loads wherein metal is under friction, undergo metal to metal contact even when being lubricated. Thus, there is always metal wear which can be excessive, because lubricants used to protect the metal surfaces often do not completely prevent wear at the points of metal to metal contact. Consequently, the performance of the machine or engine will suffer, and in aggravated cases the machine or engine may become completely inoperative from excessive wear caused the friction.

There have been many attempts to devise additive systems to improve the friction properties of a lubricant. The phosphate derivatives of the present invention are believed to be capable of overcoming some of the deficiencies of prior art additives and to provide lubricating oil compositions with enhanced friction characteristics.

U.S. Pat. No. 2,758,971 describes a class of metal phosphonates which are disclosed as having properties which prevent breakdown of oils at high temperatures.

U.S. Pat. No. 2,792,374 discloses the alkali metal salts of certain alkyl alkylphosphonic acids as defoamants in aqueous systems.

U.S. Pat. No. 2,982,727 discloses lubricating oil compositions containing certain salts of oxygen-containing esters of phosphorus. The esters are phosphonates similar to those described in U.S. Pat. No. 2,758,971.

U.S. Pat. No. 4,382,035 discloses a new glycerol-3-phosphoric acid halogenalkyl ester of the formula

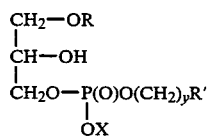

where R, R', X and y are as defined therein. Certain diols have been disclosed as having lubricity properties when formulated into lubricants and for their water-scavaging abilities in fuels. Phosphate esters are well known as functional lubricants.

The use of boron containing compositions has also been widely reported. Borates and borate esters are disclosed in U.S. Pat. Nos. 4,370,248; 4,298,486 and 4,273,665.

Many phosphorus containing additives have found widespread use in the past. Phosphonates have been used as lubricity agents as exemplified by Papay in U.S. Pat. No. 4,356,097 in his disclosure of dihydrocarbyl hydrocarbyl phosphonate containing lubricant compositions.

Certain long chain vicinal diols are disclosed in U.S. Pat. Nos. 3,649,358 and 3,899,433.

However, no art is known that teaches or suggests the phosphate ester of the present invention.

The use of these novel borates of diol-derived partial phosphate esters in lubricants provide effective multifunctional friction reducing, antioxidant, antiwear and copper passivating activity, with potential antifatigue and grease high temperature stabilizing properties. These unique phosphate ester-derived borated diols provide greater potential antiwear activity than previously reported alkanediols and greater friction reducing properties than previously reported phosphate esters.

SUMMARY OF THE INVENTION

In accordance with the invention, there are provided a product of reaction made by reacting a phosphorus oxyhalide, preferably the oxychloride, a vicinal diol and a boron compound. The invention also provides a lubricant or liquid fuel composition comprising a major proportion of a lubricant or fuel and an antifriction amount of said product of reaction. Further, lubricant and fuel compositions containing the products also have fuel consumption reducing properties when used in internal combustion engines.

DESCRIPTION OF SPECIFIC EMBODIMENTS

Because of the relatively complex nature of the reaction that occurs when phosphorus oxyhalide, vicinal diols and boron compounds are interacted, no precise structure can be assigned to the product. Thus, the final product will be referred to herein, both in the specification and the claims, as the product of the specified reaction.

However, it is believed that the reaction product obtained by reacting the diol with, for example, POCl₃ comprises at least some of the following compounds:

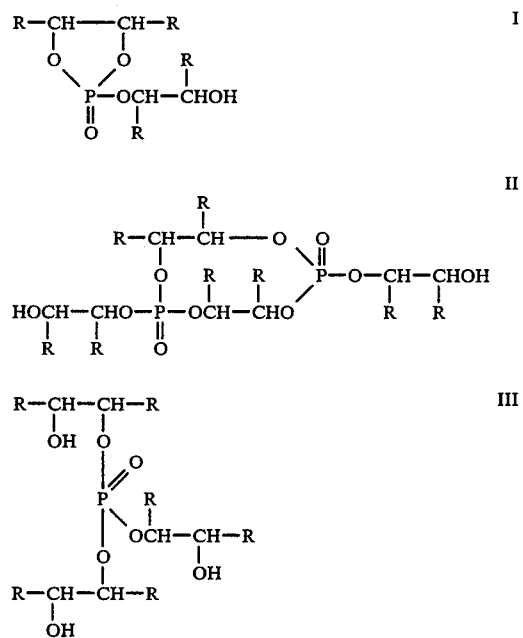

-continued

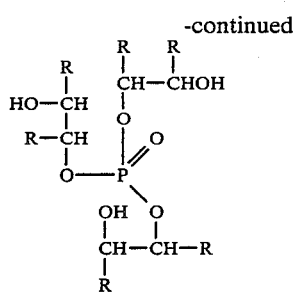
IV and oligomers thereof. R is defined hereinbelow. The depicted compounds react with boron compounds such as boric acid to give products in which one or more of the hydroxy groups are borated to give simple or increasingly complex molecules depending upon the number of hydroxy groups present for reaction. For example, Compound I can react with boric acid to produce a product in which 1, 2 or 3 of the acid groups are reacted, e.g.,

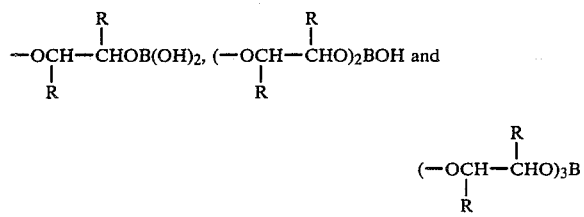

The products of reaction are preferably made by first reacting the diol with phosphorus oxyhalide, followed by reacting the product thus formed with a boron compound, preferably boric acid. Alternatively, they can be made by first partially borating the diol, and reacting this product with phosphorus oxyhalide.

The hydrocarbyl vicinal diols contemplated for use in this invention are hydrocarbyl diols having vicinal hydroxy groups. They have the formula:

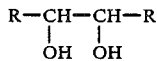

wherein R is hydrogen or a hydrocarbyl group containing 1 to 30 carbon atoms, preferably 12 to 30 carbon atoms, including mixtures thereof. At least one R is a hydrocarbyl group and can be linear or branched, saturated or unsaturated. The two hydroxy groups are preferably near the end of the hydrocarbyl chain. The hydrocarbyl groups are preferably alkyl groups, but may also be aryl, alkaryl, aralkyl, cycloalkyl groups.

Among the diols contemplated are 1,2-dodecanediol, 1,2-tetradecanediol, 1,2-pentadecanediol, 1,2-hexadecanediol, 1,2-heptadecanediol, 1,2-octadecanediol, mixed 1,2-$C_{15}$–$C_{18}$ alkanediols, and mixtures of all such diols, including mixtures of similar diols. Also included are diols prepared by the hydroxylation of olefins such as propylene tetramer, propylene pentamer, butylene trimer, similar olefins and mixtures of olefins. Mixtures are often preferred.

The vicinal diols can be synthesized using several methods known to the art. One such method, described in an article in *J. Am. Chem. Soc.*, 68, 1504 (1946), involves the hydroxylation of 1-olefins with peracids. Vicinal diols can also be prepared by the peroxytrifluoroacetic acid method for the hydroxylation of olefins as described in *J. Am. Chem. Soc.*, 76, 3742 (1954). Similar procedures can be found in U.S. Pat. Nos. 2,411,762, 2,457,329 and 2,455,892. These are incorporated herein by reference.

The diols can also be prepared via catalytic epoxidation of an appropriate olefin, followed by hydrolysis.

As disclosed hereinabove, the preferred vicinal diols contain 12 to 30 carbon atoms. This range is preferred because diols having much less than 12 carbon atoms have significantly less friction reducing properties, while in those having more than 20 carbon atoms, solubility constraints or other adverse physical effects become significant. More preferred are the $C_{14}$ to $C_{18}$ hydrocarbyl groups and mixtures of such hydrocarbyl groups in which solubility, frictional characteristics and other properties appear to be maximized.

Other additives, such as detergents, dispersants, antioxidants, antiwear agents, extreme pressure additives, pour depressants, antirust additives and the like may be present in the composition. These may include phenates, sulfonates, succinimides, zinc dialkyl and diaryl dithiophosphates, polymers, calcium and magnesium containing additives and the like. Frictional and high temperature improvements are often best in lubricants in the presence of from about 0.1 to about 5 wt. % of zinc dialkyl dithiophosphates and zinc diaryl dithiophosphates.

The useful boron compounds include boric oxide and the metaborates, as well as other boron compounds of the formula $$(R^{I}O)_{x}B(OH)_{y}$$

wherein $R^{I}$ is a $C_1$ to $C_6$ alkyl group and x and y are 0 to 3, the sum thereof being 3. Included within this formula are boric acid, mono-, di- and trimethyl borates, mono-, di- and triethyl borates, mono-, di- and tripropyl borates, mono-, di- and tributyl borates, mono-, di- and tripentyl borates and mono-, di- and trihexyl borates.

In both of the reaction schemes mentioned above, the temperature of reaction with boron is from about 80° C. to about 260° C., preferably from about 120° C. to about 180° C. and for reaction with phosphorus oxyhalide the temperature of reaction is from about 30° C. to about 220° C., preferably about 50° C. to about 160° C.

In the first reaction mentioned the diol is reacted with phosphorus oxyhalide so that from about 5% to about 95% of the hydroxy functions are reacted. The resulting phosphate is then reacted with boron compound to react from about 5% to 100% of the unphosphated hydroxy groups. Up to a 50% excess of boron compound may be used when complete boration is desired. An excess of boron is often desirable.

The alternative reaction is carried out by reacting the diol with boron compound so that about 5% to about 95% of the hydroxy groups are borated. The borated product is then reacted with enough phosphorus halide to react with from about 5% to 100% of the unborated diol hydroxy groups.

A solvent is desirable in some cases where strongly exothermic reaction occurs and generally useful for the azeotropic removal of the water formed during the condensation reaction. Where a solvent is used, it should be one in which the products are soluble and which can be relatively easily removed. Examples of some solvents that may be useful solvents are toluene, benzene, xylene, cyclohexane, hexane and the like. For the boration reaction only, alcohol solvents such as butanol or hexamethylene glycol can often be used.

Atmospheric pressure can be used, but reduced pressure is often desirable as an aid to eliminate hydrogen chloride produced during the phosphorus oxyhalide reaction. This reaction is progressed to near completion to cause almost complete elimination of halide from the products using procedures known to those skilled in this art, including time and temperature.

The compounds of the invention are used with lubricating oils or greases to the extent of from about 0.05% to about 10% by weight of the total composition, preferably from 0.1% to 5% and with fuels to the extent of from about 5 lbs. to about 250 lbs. per 1,000 bbls. of fuel. Furthermore, other additives, such as detergents, antioxidants, antiwear agents and the like may be present. These can include phenates, sulfonates, succinimides, zinc dialkyl dithiophosphates, polymers, calcium and magnesium salts of phenates and sulfonates, including overbased salts of the same, and the like.

The lubricants contemplated for use with the esters herein disclosed include mineral and synthetic hydrocarbon oils of lubricating viscosity, mixtures of mineral oils and synthetic oils and greases from any of these, including the mixtures. The synthetic hydrocarbon oils include long-chain alkanes such as cetanes and olefin polymers such as oligomers of hexane, octene, decene, and dodecene, etc. These vicinal diols are especially effective in synthetic oils formulated using mixtures of synthetic hydrocarbon olefin oligomers and lesser amounts of hydrocarbyl carboxylate ester fluids. The other synthetic oils, which can be used alone with the borated compounds of this invention, or which can be mixed with a mineral or synthetic hydrocarbon oil, include (1) fully esterified ester oils, with no free hydroxyls, such as pentaerythritol esters of monocarboxylic acids having 2 to 20 carbon atoms, trimethylolpropane esters of monocarboxylic acids having 2 to 20 carbon atoms, (2) polyacetals and (3) siloxane fluids. Especially useful among the synthetic esters are those made from polycarboxylic acids and monohydric alcohols. More preferred are the ester fluids made by fully esterifying pentaerythritol, or mixtures thereof with di- and tripentaerythritol, with an aliphatic monocarboxylic acid containing from 1 to 20 carbon atoms, or mixtures of such acids.

A wide variety of thickening agents can be used in the greases of this invention. Included among the thickening agents are alkali and alkaline earth metal soaps of fatty acids and fatty materials having from about 12 to about 30 carbon atoms per molecule. The metals are typified by sodium, lithium, calcium and barium. Fatty materials are illustrated by stearic acid, hydroxystearic acid, stearin, cottonseed oil acids, oleic acid, palmitic acid, myristic acid and hydrogenated fish oils. Often preferred are the lithium 12-hydroxystearate containing soaps.

Other thickening agents include salt and salt-soap complexes as calcium stearate-acetate (U.S. Pat. No. 2,197,263), barium stearate acetate (U.S. Pat. No. 2,564,561), calcium stearate-caprylate-acetate complexes (U.S. Pat. No. 2,999,065), calcium caprylate-acetate (U.S. Pat. No. 2,999,066), and calcium salts and soaps of low-, intermediate- and high-molecular weight acids and of nut oil acids.

Another group of thickening agents comprises substituted ureas, phthalocyanines, indanthrene, pigments such as perylimides, pyromellitdiimides, and ammeline.

The preferred thickening gelling agents employed in the grease compositions are essentially hydrophobic clays. Such thickening agents can be prepared from clays which are initially hydrophilic in character, but which have been converted into a hydrophobic condition by the introduction of long chain hydrocarbon radicals onto the surface of the clay particles prior to their use as a component of a grease composition, as, for example, by being subjected to a preliminary treatment with an organic cationic surface active agent, such as an onium compound. Typical onium compounds are tetraalkylammonium chlorides, such as dimethyl dioctadecyl ammonium chloride, dimethyl dibenzyl ammonium chloride and mixtures thereof. This method of conversion, being well known to those skilled in the art, is believed to require no further discussion, and does not form a part of the present invention. More specifically, the clays which are useful as starting materials in forming the thickening agents to be employed in the grease compositions, can comprise the naturally occurring chemically unmodified clays. These clays are crystalline complex silicates, the exact composition of which is not subject to precise description, since they vary widely from one natural source to another. These clays can be described as complex inorganic silicates such as aluminum silicates, magnesium silicates, barium silicates, and the like, containing, in addition to the silicate lattice, varying amounts of cation-exchangeable groups such as sodium. Hydrophilic clays which are particularly useful for conversion to desired thickening agents include montmorillonite clays, such as bentonite, attapulgite, hectorite, illite, saponite, sepiolite, biotite, vermiculite, zeolite clays, and the like. The thickening agent is employed in an amount from about 0.5 to about 30, and preferably from 3 percent to 15 percent by weight of the total grease composition.

The liquid fuels contemplated include the liquid hydrocarbons, such as gasoline, fuel oil and diesel oil and the liquid alcohols such as methyl alcohol and ethyl alcohol. The fuels also include mixtures of alcohols as well as mixtures of alcohols and liquid hydrocarbons.

Having described the invention in general aspects, the following examples are offered as specific illustrations. Parts are by weight.

EXAMPLE 1

Phosphate Ester of 1,2-Mixed Pentadecanediol-Octadecanediol

Approximately 240 g of 1,2-mixed pentadecanediol-octadecanediol (obtained as Vikol 158 from Viking Chemical Co. and containing by weight about 28% 1,2-pentadecanediol, 28% 1,2-hexadecanediol, 28% 1,2-heptadecanediol and 16% 1,2-octadecanediol) was heated to about 60° C. in a glass reactor equipped with agitator and provision for reducing the pressure to 1/10 atmosphere. Over a period of about 1 hour, 35 g of phosphorus oxychloride ($POCl_3$) were added dropwise while maintaining a temperature of 70°-75° C., and reduced pressure. The reaction mixture was then held at 85°-90° C. for 6 additional hours at reduced pressure until evolution of hydrogen chloride ceased. The product was a pale amber fluid which became waxy upon cooling.

EXAMPLE 2

Partially Borated, Partial Phosphate Ester of 1,2-Mixed Pentadecanediol-Octadecanediol Approximately 120 g of the product of Example 1, 100 g of toluene and 5 g of boric acid were charged to a 1 liter flask equipped with heater, agitator, provision for maintaining nitrogen atmosphere and Dean-Stark tube with condenser. The reaction mixture was heated up to 155° C. with water evolution, as a result of azeotropic distillation, ceased. A total of 4½ ml water was collected. The solvent was removed by vacuum topping at 155° C. and the product was filtered at about 120° C. through diatomaceous earth. The product was a clear amber liquid which became waxy after cooling.

EXAMPLE 3

Partially Borated, Partial Phosphate Ester of 1,2-Mixed Pentadecanediol-Octadecanediol Approximately 123 g of the product of Example 1, 100 g of toluene and 10 g of boric acid were charged to a reactor equipped as generally described in Example 2. The reactants were heated up to 155° C. until water evolution, as a result of azeotropic distillation, ceased. The solvent was removed by vacuum topping at about 155° C. and the product was filtered at about 120° C. through diatomaceous earth. The product was a clear amber liquid which became waxy upon cooling.

EXAMPLE 4

Partial Phosphate Ester of 1,2-Mixed-Pentadecanediol-Octadecanediol

Approximately 240 g of the 1,2-mixed-pentadecanediol-octadecanediol of Example 1 were heated to about 60° C. in a glass reactor equipped with agitator and provision for reducing the pressure to 1/10 atmosphere. Over a period of one hour, 52 g of phosphorus oxychloride were added dropwise while maintaining a temperature of 68°-70° C. at reduced pressure. The reaction mixture was then held at 80° C. for seven additional hours at reduced pressure until evolution of hydrogen chloride ceased. The product was a pale amber fluid which became waxy upon cooling.

EXAMPLE 5

Partially Borated, Partial Phosphate Ester of 1,2-Mixed Pentadecanediol-Octadecanediol Approximately 125 g of the product of Example 4, 100 g of toluene and 10 g of boric acid were changed to a reactor equipped as generally described in Example 2. The reaction mixture was heated up to 150° C. until water evolution, as a result of azeotropic distillation, ceased. The solvent was removed by vacuum topping at 150° C. and the crude product were filtered at about 120° C. through diatomaceous earth. The product was a clear amber liquid which became waxy upon cooling.

EXAMPLE 6

Partial Phosphate Ester of 1,2-Mixed-Pentadecanediol-Octadecanediol

Approximately 240 g of the 1,2-mixed-pentadecanediol-octadecanediol of Example 1 were heated to about 65° C. in a glass reactor equipped with agitator and provision for reducing the pressure to 1/10 atmosphere. Over a period of 1 hour, 23 g of phosphorus oxychloride were added dropwise while maintaining a temperature of 65°-70° C. The reaction mixture was then held at 90°-95° C. for seven additional hours at reduced pressure until evolution of hydrogen chloride ceased. The product was a pale amber fluid which became waxy upon cooling.

EXAMPLE 7

Partially Borated, Partial Phosphate Ester of 1,2-Mixed Pentadecanediol-Octadecanediol Approximately 125 g of the product of Example 6, 100 g of toluene and 15 g of boric acid were changed to a reactor equipped as generally described in Example 2. The reaction mixture was heated up to 150° C. until water evolution, as a result of azeotropic distillation, ceased (about 7 hours). The solvent was removed by vacuum topping at about 150° C. and the product was filtered at about 120° C. through diatomaceous earth. The product was a clear amber liquid which became waxy upon cooling.

EXAMPLE 8

Partial Phosphate Ester of 1,2-Dodecanediol

Approximately 278 g of the 1,2-dodecanediol (obtained as Vikol 12 from Viking Chemical Co.) were heated to about 60° C. in a glass reactor equipped with agitator and provision for reducing the pressure to about 1/10 atmosphere. Over a period of about one hour, 76 g of phosphorus oxychloride was added dropwise while maintaining a temperature of about 70°-75° C. and reduced pressure. The reaction mixture was then held at about 105° C. for five additional hours at reduced pressure until evolution of hydrogen chloride ceased. The product was a pale amber fluid which became waxy upon cooling.

EXAMPLE 9

Partially Borated, Partial Phosphate Ester of 1,2-Dodecanediol

Approximately 120 g of the product of Example 8, 100 g of toluene and 10.5 g of boric acid were changed to a reactor equipped as generally described in Example 2. The reaction mixture was heated up to 155° C. until water evolution, as a result of azeotropic distillation, ceased. More than 7 ml of water collected. The solvent was removed by vacuum stripping at about 155° C. and the product was filtered at about 110° C. through diatomaceous earth. The product was a clear amber fluid which became waxy upon cooling.

The borate/phosphate esters were blended into fully formulated synthetic and mineral oil based engine oil lubricants and evaluated using the Low Velocity Friction Apparatus Test. These formulations included polymeric dispersants, metallic phenates and sulfonates, zinc dithiophosphates and polymeric viscosity index improving additives. As the data, given hereinbelow shows, the use of only 1% of the product of Example 2 reduced the coefficient of friction by 48% as shown in Table 1.

LOW VELOCITY FRICTION APPARATUS

Description

The Low Velocity Friction Apparatus (LVFA) is used to measure the friction of test lubricants under various loads, temperatures, and sliding speeds. The LVFA consists of a flat SAE 1020 steel surface (diam. 1.5 in.) which is attached to a drive shaft and rotated over a stationary, raised, narrow ringed SAE 1020 steel surface (area 0.08 in.$^2$). Both surfaces are submerged in the test lubricant. Friction between the steel surfaces is measured as a function of the sliding speed at a lubricant temperature of 250° F. The friction between the rubbing surfaces is measured using a torque arm-strain gauge system. The strain gauge output, which is calibrated to be equal to the coefficient of friction, is fed to the Y axis of an X-Y plotter. The speed signal from the tachometer-generator is fed to the X-axis. To minimize external friction, the piston is supported by an air bearing. The normal force loading the rubbing surfaces is regulated by air pressure on the bottom of the piston. The drive system consists of an infinitely variable-speed hydraulic transmission driven by a ½ HP electric motor. To vary the sliding speed, the output speed of the transmission is regulated by a lever-cam motor arrangement.

PROCEDURE

The rubbing surfaces and 12-13 ml of test lubricant are placed on the LVFA. A 240 psi load is applied, and the sliding speed is maintained at 40 fpm at ambient temperature for a few minutes. A plot of coefficients of friction ($U_k$) over the range of sliding speeds, 5 to 40 fpm (25-195 rpm), is obtained. A minimum of three measurements is obtained for each test lubricant. Then, the test lubricant and specimens are heated to 250° F., another set of measurements is obtained, and the system is run for 50 minutes at 250° F., 240 psi and 40 fpm sliding speed. Afterward, measurements of $U_k$ vs. speed are taken at 240, 300, 400, and 500 psi. Freshly polished steel specimens are used for each run. The surface of the steel is parallel ground to 4-8 microinches.

The results obtained are shown in Tables 1 and 2. The data in the tables are reported as percent reduction in coefficient of friction at two speeds. The friction-reducing ester additives were evaluated in a fully formulated 5W-30 synthetic lubricating oil (Table 1) or 10W-40 mineral lubricating oil (Table 2), each comprising an additive package including antioxidant, detergent and dispersant.

TABLE 1

Friction Test Results Using The Low Velocity Friction Apparatus

| | Additive Conc. in Base Fluid Wt % | % Reduction In Coefficient Of Friction @ | |
|---|---|---|---|
| | | 5 Ft/Min | 30 Ft/Min |
| Base Oil A (fully formulated synthetic automotive engine oil containing detergent/ dispersant inhibitor performance package SAE 5W-30 | — | 0 | 0 |
| Example 2 Plus Base Oil | 1 | 48 | 41 |
| | 0.5 | 26 | 23 |
| Example 3 Plus Base Oil | 1 | 34 | 24 |
| Example 7 Plus Base Oil | 1 | 43 | 33 |
| | 0.5 | 29 | 23 |
| Example 9 Plus Base Oil | 1 | 17 | 13 |

TABLE 2

Friction Test Results Using The Low Velocity Friction Apparatus

| | Additive Conc. in Base Fluid Wt % | % Reduction In Coefficient Of Friction @ | |
|---|---|---|---|
| | | 5 Ft/Min | 30 Ft/Min |
| Base Oil B (fully formulated mineral oil based automotive engine oil containing detergent/dispersant/inhibitor performance package SAE 10W-40 | — | 0 | 0 |
| Example 2 Plus Base Oil | 1 | 34 | 28 |
| Example 5 Plus Base Oil | 1 | 23 | 23 |
| Example 7 Plus Base Oil | 1 | 26 | 20 |
| Example 9 Plus Base Oil | 1 | 20 | 16 |

COPPER CORROSION TEST

Copper strip corrosivity properties of the additives of the invention were measured by testing the compositions in 200" Solvent Paraffinic Neutral (SPN) mineral lubricating oil as directed in ASTM D130-80. The data are shown in Table 3.

TABLE 3

Copper Strip Corrosivity Test Results

| | Conc. of Additive % | ASTMD130-80 3 Hrs @ 250° F. | ASTMD130-80 6 Hrs @ 210° F. |
|---|---|---|---|
| Example 2 Plus Oil | 0.5 | 1A | 1A |
| Example 3 Plus Oil | 0.5 | 1A | 1A |
| Example 5 Plus Oil | 0.5 | 1A | 1A |
| Example 7 Plus Oil | 0.5 | 1A | — |
| Example 9 Plus Oil | 0.5 | 1A | — |

CATALYTIC OXIDATION TEST

The test lubricant composition was subjected to a stream of air which is bubbled therethrough at a rate of 5 liters per hour at 325° F. for 40 hours. Present in the composition are metals commonly used in the construction of engines. These are sand-blasted iron wire, polished copper wire, polished aluminum wire and polished lead. The oil used was a 200" SPN mineral oil. Table 4 has the results of the test.

TABLE 4

Catalytic Oxidation Test

| | Additive Conc. Wt. % | % Increase in Viscosity of Oxidized Oil Using KV @ 100° F. | Neut. Number |
|---|---|---|---|
| Base Oil, 200" solvent paraffinic Neutral Lubricating Oil | 0 | 67 | 3.62 |
| Example 2 Plus Base Oil | 1.0 | 20 | 3.96 |
| Example 3 Plus Oil | 0.5 | 27 | 3.23 |
| Example 5 Plus Oil | 0.5 | 24 | 3.08 |
| Example 7 Plus Oil | 0.5 | 18 | 2.83 |

We claim:

1. A product of reaction made by reacting a vicinal diol, a phosphorus oxyhalide and a boron compound, the vicinal diol being reacted with the phosphorus oxyhalide at a temperature between about 30° C. to about 220° C. in sufficient quantity so that about 5% to about 95% of the diol hydroxy functions are reacted, and the product thereby obtained being reacted with the boron compound at a temperature between about 80° C. and about 260° C. in sufficient quantity so that between about 5% and about 100% of the unreacted hydroxy functions are reacted, or the vicinal diol being reacted with the boron compound at a temperature between about 80° C. and about 260° C. in sufficient quantity so that about 5% to about 95% of the diol hydroxy functions are reacted, and the product thereby obtained being reacted with the phosphorus oxyhalide at a temperature between about 30° C. and about 220° C. in sufficient quantity so that about 5% to about 100% of the unreacted hydroxy functions are reacted, all reactions being conducted at a pressure between about atmospheric and less than atmospheric pressure.

2. The product of claim 1 wherein the vicinal diol has the formula

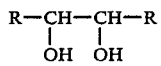

wherein R is hydrogen or the same or different $C_1$ to $C_{30}$ hydrocarbyl group, at least one of them being hydrocarbyl.

3. The product of claim 1 wherein the phosphorus oxyhalide is phosphorus oxychloride.

4. The product of claim 1 wherein the boron compound is boric oxide, a metaborate or a compound of the formula

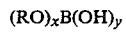

wherein R is a $C_1$ to $C_6$ alkyl group and x and y are 0 to 3, their sum being 3.

5. The product of caim 2 wherein the diol is selected from the group consisting of 1,2-dodecanediol, 1,2-tetradecanediol, 1,2-pentadecanediol, 1,2-hexadecanediol, 1,2-heptadecanediol, 1,2-octadecane diol, mixed 1,2-$C_{15}$–$C_{18}$ alkanediols and mixtures of any of the named diols.

6. The product of claim 4 wherein the boron compound is a boric acid.

7. The product of claim 4 wherein the boron compound is selected from the group consisting of mono-, di- or trimethyl borates, mono-, di- or trimethyl borates, mono-, di- or tripropyl borates, mono-, di- or tributyl borates, mono-, di- or tripentyl borates and mono-, di- or trihexyl borates.

8. The product of claim 1 wherein the diol is 1,2-mixed pentadecanediol-octadecanediol, the phosphorus oxyhalide is phosphorus oxychloride and the boron compound is boric acid.

9. The product of claim 1 wherein the diol is 1,2-dodecanediol, the phosphorus oxyhalide is phosphorus oxychloride and the boron compound is a boric acid.

10. A lubricant comprising a major amount of a lubricant selected from the group consisting of (1) a mineral oil, (2) a synthetic oil or a mixture of synthetic oils, (3) a mixture of (1) and (2) and (4) a grease from any of (1), (2) and (3) and an antifriction amount of a product of reaction made by reacting a vicinal diol, a phosphorus oxyhalide and a boron compound, the vicinal diol being reacted with the phosphorus oxyhalide at a temperature between about 30° C. to about 220° C. in sufficient quantity so that about 5% to about 95% of the diol hydroxy functions are reacted, and the product thereby obtained being reacted with the boron compound at a temperature between about 80° C. and about 260° C. in sufficient quantity so that between about 5% and about 100% of the unreacted hydroxy functions are reacted, or the vicinal diol being reacted with the boron compound at a temperature between about 80° C. and about 260° C. in sufficient quantity so that about 5% to about 95% of the diol hydroxy functions are reacted, and the product thereby obtained being reacted with the phosphorus oxyhalide at a temperature between about 30° C. and about 220° C. in sufficient quantity so that about 5% to about 100% of the unreacted hydroxy functions are reacted, all reactions being conducted at a pressure between about atmospheric and less than atmospheric pressure.

11. The composition of claim 10 wherein the vicinal diol has the formula

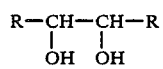

wherein R is hydrogen or the same or different $C_1$ to $C_{30}$ hydrocarbyl group, at least one of them being hydrocarbyl.

12. The composition of claim 10 wherein the phosphorus oxyhalide is phosphorus oxychloride.

13. The composition of claim 10 wherein the boron compound is boric oxide, a metaborate or a compound of the formula

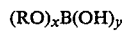

wherein R is a $C_1$ to $C_6$ alkyl group and x and y are 0 to 3, their sum being 3.

14. The composition of claim 11 wherein the diol is selected from the group consisting of 1,2-dodecanediol, 1,2-tetradecanediol, 1,2-pentadecanediol, 1,2-hexadecanediol, 1,2-heptadecanediol, 1,2-octadecane diol, mixed 1,2-$C_{15}$–$C_{18}$ alkanediols and mixtures of any of the named diols.

15. The composition of claim 13 wherein the boron compound is a boric acid.

16. The composition of claim 13 wherein the boron compound is selected from the group consisting of mono-, di- or trimethyl borates, mono-, di- or trimethyl borates, mono-, di- or tripropyl borates, mono-, di- or tributyl borates, mono-, di- or tripentyl borates or mono-, di- or trihexyl borates.

17. The composition of claim 10 wherein the diol is 1,2-mixed pentadecanediol-octadecanediol, the phosphorus oxyhalide is phosphorus oxychloride and the boron compound is boric acid.

18. The composition of claim 10 wherein the diol is 1,2-dodecanediol, the phosphorus oxyhalide is phosphorus oxychloride and the boron compound is a boric acid.

19. The composition of claim 10 wherein the lubricant is a mineral oil.

20. The composition of claim 10 wherein the lubricant is a synthetic oil or mixture of synthetic oils.

21. The composition of claim 10 wherein the lubricant is as designated in (3).

22. The composition of claim 10 wherein the lubricant is a grease.

23. The composition of claim 10 wherein the lubricant additionally has therein one or more additives selected from metallic dithiophosphates, metallic sulfonates and metallic phenates.

24. The composition of claim 23 wherein the metallic dithiophosphate is zinc dialkyl dithiophosphate or zinc diaryl dithiophosphate, present therein in a concentration of from about 0.1 to about 5% by weight.

25. The composition of claim 23 wherein said grease is thickened with a metal hydroxystearate and contains a metal dialkyl or diaryl dithiophosphate.

26. The composition of claim 25 wherein said metal hydroxystearate is lithium 12-hydroxystearate and said metal dialkyl or diaryl dithiophosphate is zinc dialkyl or diaryl dithiophosphate.

27. A method for reducing fuel consumption in an internal combustion engine which comprises lubricating said engine with a lubricant composition comprising a major amount of a lubricating oil and a fuel reducing amount of a product of reaction of claim 1.

* * * * *